(12) United States Patent  
Linguraru et al.

(10) Patent No.: US 9,370,318 B2  
(45) Date of Patent: Jun. 21, 2016

(54) QUANTITATIVE ASSESSMENT OF THE SKULL

(71) Applicants: Marius G. Linguraru, Washington, DC (US); Carlos S. Mendoza, Washington, DC (US); Nabile Safdar, Laurel, MD (US); Gary F. Rogers, Great Falls, VA (US)

(72) Inventors: Marius G. Linguraru, Washington, DC (US); Carlos S. Mendoza, Washington, DC (US); Nabile Safdar, Laurel, MD (US); Gary F. Rogers, Great Falls, VA (US)

( * ) Notice: Subject to any disclaimer, the term of this patent is extended or adjusted under 35 U.S.C. 154(b) by 272 days.

(21) Appl. No.: 14/046,656

(22) Filed: Oct. 4, 2013

(65) Prior Publication Data

US 2014/0100485 A1 Apr. 10, 2014

Related U.S. Application Data

(60) Provisional application No. 61/709,727, filed on Oct. 4, 2012.

(51) Int. Cl.
*A61B 5/107* (2006.01)
*A61B 6/00* (2006.01)
(Continued)

(52) U.S. Cl.
CPC ............. *A61B 5/1075* (2013.01); *A61B 5/7246* (2013.01); *A61B 6/501* (2013.01);
(Continued)

(58) Field of Classification Search
CPC .... A61B 5/107; A61B 5/1075; A61B 5/7246; A61B 6/03; A61B 6/032; A61B 6/501; A61B 6/5217; A61B 19/50; A61B 2019/501; A61B 2019/505; Y10S 128/92; Y10S 128/922–128/925; G06T 7/0012; G06T 7/0014; G06T 7/0016; G06T 17/00; G06T 17/20; G06T 17/205; G06T 17/30; G06T 17/10; G06T 2207/30004; G06T 2207/30008; G06T 2207/30016; G06T 2207/10081; G06T 2207/20076

USPC .................. 600/300, 301, 416, 425, 427, 587; 128/897, 898, 920, 922–925; 703/1, 703/11; 382/128, 131; 345/419, 423
See application file for complete search history.

(56) References Cited

U.S. PATENT DOCUMENTS

| | | | | |
|---|---|---|---|---|
| 7,953,260 | B2 * | 5/2011 | Weinzweig et al. | 382/128 |
| 8,425,229 | B2 * | 4/2013 | Nilsson et al. | 433/172 |
| 2008/0030497 | A1 * | 2/2008 | Hu et al. | 345/419 |
| 2009/0128553 | A1 * | 5/2009 | Perry et al. | 382/131 |

OTHER PUBLICATIONS

Mendoza et al. "Personalized assessment of craniosynostosis via statistical shape modeling." Medical image analysis 18.4 (2014): 635-646.*

(Continued)

*Primary Examiner* — Devin Henson
*Assistant Examiner* — David J McCrosky
(74) *Attorney, Agent, or Firm* — Oblon, McClelland, Maier & Neustadt, L.L.P.

(57) ABSTRACT

A technique for performing computational analysis of craniosynostosis from CT images is discussed. An image-computing platform assesses craniofacial malformations by using a shape analysis methodology for image processing. The shape of a patient's craniofacial anatomy is assessed in terms of a statistical shape model that incorporates normal shape variability. The model allows for the identification of a closest normal variant to a patient's anatomy rather than comparing the patient's anatomy to an age-specific average shape. Further, an image registration and segmentation method is discussed which enables obtaining a personalized anatomical model for each patient, thereby achieving a precise and systematic characterization of shape abnormality. Visual (qualitative) and quantitative surgical planning, as well as pre-operative and post-operative assessments are achieved. Further, automatic surgical planning for cranial vault reconstruction using tessellation algorithms to establish the relationship between patient's anatomy and the closest normal variant is discussed.

29 Claims, 5 Drawing Sheets
(1 of 5 Drawing Sheet(s) Filed in Color)

(51) Int. Cl.
  A61B 5/00   (2006.01)
  G06T 7/00   (2006.01)
  A61B 19/00  (2006.01)
  A61B 6/03   (2006.01)
(52) U.S. Cl.
  CPC .......... *A61B 6/5217* (2013.01); *G06T 7/0014* (2013.01); *A61B 6/03* (2013.01); *A61B 2019/501* (2013.01); *A61B 2019/505* (2013.01); *G06T 2207/10081* (2013.01); *G06T 2207/20076* (2013.01); *G06T 2207/30008* (2013.01); *Y10S 128/922* (2013.01); *Y10S 128/923* (2013.01)

(56) References Cited

OTHER PUBLICATIONS

Mendoza, et al. "An optimal set of landmarks for metopic craniosynostosis diagnosis from shape analysis of pediatric CT scans of the head." SPIE Medical Imaging. International Society for Optics and Photonics, 2013.*

Mendoza, et al. "Computer-based quantitative assessment of skull morphology for craniosynostosis." Clinical Image-Based Procedures. From Planning to Intervention. Springer Berlin Heidelberg, 2013. 98-105.*

Lamecker, et al. "Surgical treatment of craniosynostosis based on a statistical 3D-shape model: First clinical application." International Journal of Computer Assisted Radiology and Surgery 1 (2006): 253.*

Liu, et al. "Interactive separation of segmented bones in CT volumes using graph cut." Medical Image Computing and Computer-Assisted Intervention—MICCAI 2008. Springer Berlin Heidelberg, 2008. 296-304.*

Ruiz-Correa, et al. "A bayesian hierarchical model for classifying craniofacial malformations from ct imaging." Engineering in Medicine and Biology Society, 2008. EMBS 2008. 30th Annual International Conference of the IEEE. IEEE, 2008.*

Kellogg, et al. "Interfrontal angle for characterization of trigonocephaly: part 1: development and validation of a tool for diagnosis of metopic synostosis." Journal of Craniofacial Surgery 23.3 (2012): 799-804.*

* cited by examiner

QUANTITATIVE ASSESSMENT OF THE SKULL

INCORPORATION BY REFERENCE

This disclosure claims the benefit of U.S. Provisional Application No. 61/709,727, filed on Oct. 4, 2012, the disclosure of which is incorporated herein by reference in its entirety.

FIELD OF INVENTION

The present disclosure relates to pediatric reconstructive surgery in craniofacial and orthopedic interventions. Specifically, methods to achieve rapid and accurate radiographic diagnosis, improvements in severity assessment, and direct planning for operative interventions are discussed. Moreover, the methods can be applied to other types of reconstructive surgery and implant design where the assessment of deformity of a shape of an organ/object and a reconstructive surgical plan is critical.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

3D computed tomography (CT) is the de-facto imaging standard for assessment of craniofacial malformation. Previous clinical studies have attempted to quantitatively analyze the different deformities of the skull. The studies rely on traditional anthropometric indices that are derived from linear measurements. However, such studies fail to provide a satisfactory representation of 3D skull morphology.

Shape analysis is another technique for assessing craniofacial malformations. For example, the use of point characterization along two dimensional profiles and the use of 3D point descriptions of the skull surface have been popularized. Such approaches require the surfaces of the skulls under study to be either sampled in accordance to a common geometric parameterization or sampled independently and subsequently aligned. The average skull morphology is then computed from the samples. Note that since the main goal of such works is the construction of a surgical template, the shape model is adjusted to only fit a set of linear measurements obtained from the subject.

A limitation of the above stated methodologies is the imposition of a "best-fit" or alignment dimensionality of a patient's CT scans only to those within the age group of the patient. Such techniques tend to be restrictive in that they ignore the possibility that one subject might be better represented by another age group after scale correction. It is desirable to have a computing platform that performs craniofacial diagnosis, severity assessment and surgical planning. Specifically, it is desirable that the process of diagnosis through surgical planning be automatic from start to finish. In other words, from the input of a patient's 3D CT data, the fusion status of the sutures, the severity of deformation, the true nearest normal solution, and the precise surgical intervention to achieve such, should readily follow.

Moreover another disadvantage in the prior shape analysis techniques is the means by which alignment metrics are determined. Specifically, the prior techniques employ either distance minimization between simplified segments of the skull surface or multiple user selected landmarks in order to define alignment, respectively. The former incorporates the malformed region into the alignment criteria which may be deficient for asymmetric malformations while the latter can result in a generally poor description of the anatomical requirements for alignment.

The definition of normal anatomy is another distinguishing feature between the prior methods. Some approaches use a normal shape model that is age and sex specific, comprised of twenty two groups. The model of normality is defined as the average distance from the dorsum-sella and its standard deviation at each point. However, such approaches assume that the shape variation occurs according to a fixed parameterization, an overly simplistic assumption. In other approaches, a tailored, artificial normal shape is defined that is adapted to the anatomy of the patient, using a statistical shape model derived from only twenty one scans. This shape model is tailored to a finite set of linear measurements that do not represent the full 3D geometry of the patient.

In addition to formalizing a definition of normal anatomy, determination of shape features (local characterization of shape on the skull surface) is also desired. Previous works compute abnormality using a statistical deviation from the average model at each point. However this method does not incorporate curvature features, which are particularly useful for metopic diagnosis. Such methods also rely heavily on arguable point correspondence and lack distance measurements (e.g., millimeters) that are required for surgical planning.

Furthermore, prior methods rely exclusively on age-appropriate average shape to evaluate deviations from "normal", regardless of whether these models offer the best remodeling option for the surgeon. Accurate assessment or diagnosis of the degree of deformity in craniofacial disorders is a common goal of many prior works. However, previous works arbitrarily define a set of triangles on the surface of the skull and use these geometric relationships for diagnosis. Since these techniques are based neither upon shape analysis or modeling of abnormal anatomy, the results are suboptimal. Note that, if models of abnormality are available, the abnormality models may offer distinct advantages in understanding anatomical deformation in specific clinical conditions such as craniosynostosis which could lead to better assessment protocols.

As a complete and accurate assessment of dysmorphic and normal shape is a requisite for anatomy-normalizing surgical interventions, visualization schemes that illustrate the volumetric deviation of patient to "normal" play a significant role in assisting the surgeon. However, prior efforts in craniosynostosis techniques produce a visualization that do not represent physical measurements, but statistical ones, and also do not delineate the bones and sutures. This limits the application of previous teachings in applicability for surgical planning.

SUMMARY

The present disclosure provides for an image computing platform that assesses craniofacial malformations by means of a novel shape analysis methodology for image processing including receiving, into a processor, radiological input data displaying craniofacial anatomy of a plurality of subjects, the plurality of subjects including both normal and abnormal subjects. For each of the subjects, the processing delineates bone tissue, registers the bone tissue to a reference space, and identifies craniofacial bones. The process computes a shape model from the identified craniofacial bones of the normal subjects, and, for each of the subjects, uses the shape model to identify a normal shape closest to that of the subject and computes local shape difference between the subject and the closest normal shape. For each of the abnormal subjects, the shape analysis results are classified according to different pathology types to forma a chart of a degree of local shape abnormality for each pathology and the chart is used to diagnose a pathology.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Various embodiments of this disclosure that are provided as examples will be described in detail with reference to the following figures, wherein like numerals reference like elements, and wherein.

DETAILED DESCRIPTION OF EMBODIMENTS

Figure 1:
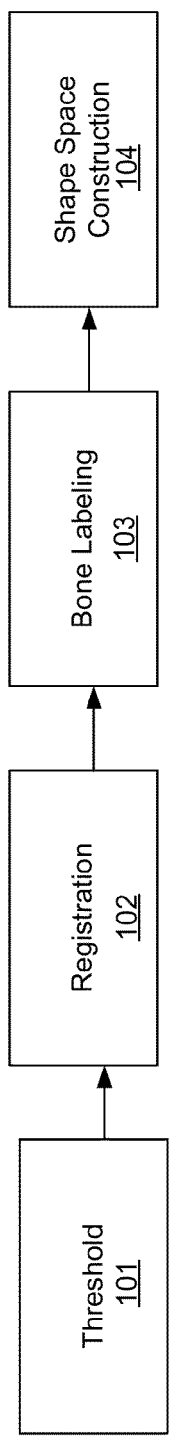
FIG. 1 is a flow diagram depicting the steps performed for obtaining a shape model.

Craniosynostosis is a congenital condition characterized by premature fusion of the cranial sutures. The incidence is 1 in 2100-2500 live births. It is usually detected early in life, both due to its cosmetic manifestations and functional consequences, as it can result in limited brain growth, elevated intra-cranial pressure, and respiratory and visual impairment. Early diagnosis is crucial for management, prevention of complications, and consideration for early surgical correction. Furthermore, as the infant brain increases in size rapidly during the first year of life, volume expansion results in compensatory areas of cranial overgrowth and abnormal morphology.

Craniosynostosis is defined as a pre-maturely fused cranial suture. It results in characteristic cranial shape changes that correlate with the specific sutural fusion: sagittal (scaphocephaly), coronal (anterior plagiocephaly), metopic (trigonocephaly) and lambdoid (posterior plagiocephaly). Shape abnormality can also occur without pathological suture fusion and it is often addressed by behavioral adjustments or mechanical devices, without surgical correction. Although the diagnosis of craniosynostosis rests on the presence of a suture fusion (the exception being metopic craniosynostosis, which depends on the severity of trigonocephaly), assessing the need for and type of surgical intervention requires consideration of several clinical factors, including the subjective evaluation of cranial shape and the degree of malformation. The surgical procedure itself is conditioned on the severity of shape abnormality in the different bones which comprise the cranial vault. Surgery can involve significant morbidity since the scalp is retracted, much of the cranium is resected, and the bone segments are reshaped and repositioned to achieve the desired configuration. Thus, it is desirable to rely on objective quantitative descriptions of shape abnormality to assist in the decision making process.

The clinical assessment of severity and need for intervention, surgical planning and intraoperative/postoperative assessment of shape in craniofacial malformations is often undertaken in a highly subjective fashion, strongly relying on the surgeon's training, experience, and craftsmanship. Image processing of 3D images has emerged as a powerful tool for understanding the anatomy of craniofacial malformation. However, there is a need for a fully automated clinical assessment and surgical planning tool (platform) that can reduce time, subjectivity of assessment and planning, quantitative guidance for minimally invasive surgical intervention, and post-operative assessment of outcome.

Accordingly, an embodiment of the present disclosure provides a method to create a statistical shape model that assesses craniofacial malformations. According to the embodiment, complete automation of steps from patient's data input to diagnostic assessment, to surgical planning and guidance, and to assessment of outcome is obtained. Further, the method provisions for increased sensitivity and specificity by incorporating a normalization technique, wherein only the bones at the base of the skull are used to align objects. The statistical shape model performs characterization of patients with respect to the closest normal variant, rather than using an age specific mean shape reference. Thus, normal anatomical variability (e.g. ethnicity) is achieved. Furthermore, because of the manner in which the shape model is constructed, the shape model also accounts for scale variations due to aging.

According to another embodiment, there is provided a method to automatically identify and label the different regions of the skull, thus improving the specificity in the analysis of shape. The embodiment provides for surgical planning and assessment based on differences between a patient's data and its closest variant. Furthermore, the ability to create systematic and quantitative models of abnormal anatomy that define robust diagnostic methods (e.g., for metopic craniosynostosis), facilitate preoperative planning, and potentially allow intraoperative and postoperative assessment of surgical outcomes, are also achieved.

Another embodiment provides a methodology for developing robust, reproducible radiographic diagnostic methods for craniofacial malformation, derived from the modelization of shape abnormality in each type of pathology. This method also gives rise to computationally-derived craniofacial reconstruction schemes, using the available shape, the closest normal shape, and a method to automatically tessellate one shape into the other resulting in increased reproducibility and specificity of craniofacial surgical reconstructions.

Specific advantages of the embodiments include the potential to impact the clinical processing of craniosynostosis. Specifically, the diagnosis of metopic craniosynostosis, and the severity assessment of all types of craniosynostosis can be performed by using the statistical shape model. Embodiment(s) of the present disclosure provide for deciding the type of surgery and aiding in planning the surgical management of craniosynostosis, including the automatic optimization of the cranial vault reconstruction to most closely approximate normal. Further, a quantitative description of the synostotic skull is provided so as to ultimately provide fully automatic diagnosis.

The proposed shape model can assess the presence of fusion of the main sutures involved in any of the types of craniosynostosis using a full 3D analysis of shape that can quantify deformation according to a precise segmentation of the bone segments in the skull. The resulting shape features are computed in reference to normal subjects mapped into a statistical shape space, producing a comparison that is tailored to the subject under study, thus producing an analysis which is less sensitive to normal variations in patient anatomy.

In what follows, a brief description of the features provided by the embodiments is first described and then a detailed description of the embodiments is provided. Specific features of the embodiments include:

Full automation capability: the craniosynostosis assessment process starting from the input of a patient's 3D CT data, evaluating the severity of deformation, finding the true nearest normal solution, and the precise surgical intervention to achieve the nearest normal solution is fully automated.

Alignment dimensionality: age differences are accounted for by scale corrections in an alignment procedure (to be described). Further, normality is regarded as a shape concept disregarding scale and sex. This allows more flexibility to move between age groups. The statistical shape model handles variations of shape due to age.

Alignment metrics: refers to the alignment of a patient's 3D CT data to the closest normal variant, where the full base of the skull is used for finding the best alignment, thus exploiting the maximum amount of reliable information, and not being affected by asymmetric malformation of the skull region.

Definition of normal anatomy: the normal reference for a given patient is the anatomy of the closest normal variant in the statistical shape space. This model encompasses normal shape variations, i.e. ethnicity. Furthermore, it exploits the full anatomy of the skull in a parameter-free manner for performing the shape matching.

Shape Features: two types of shape features are defined densely on the surface of the patient's skull. First, the physical distance from the normal reference (in millimeters); secondly, absolute curvature difference from the normal reference. Curvature allows for characterization of ridging (e.g. at the metopic suture).

Automatic delineation of bone segments: the diagnostic features are inscribed on tailored descriptions of bony anatomy. This benefits specificity of diagnosis and is relevant to surgical planning (to assess the involvement of the patient's various bone segments).

Automatic delineation and assessment of sutures: the suture regions are automatically delineated and their fusion status is automatically determined. This improves the specificity of diagnosis based on features that are local to the suture region (e.g. the ridging of the metopic suture in craniosynostosis) and also because suture fusion is the main diagnostic feature in craniosynostosis.

Models of abnormality: according to an embodiment, a methodology for building models of malformation is demonstrated. This is achieved from bone/suture segmentation and statistical analysis of shape features. In doing so, good diagnostic protocols for the different types of cranial malformation is obtained and an improved understanding of the anatomy of craniosynostosis patients is developed which provides better assessment protocols.

Diagnostic protocols: using the abnormality model together with the bone/suture automatic delineation, an embodiment of the disclosure determines the best landmarks for the diagnosis of metopic craniosynostosis in a systematic way. As result a very simple, robust, optimally derived radiographic diagnostic method for metopic craniosynostosis is obtained, in which the fusion of the suture is not indicative of craniosynostosis.

Visualization scheme: according to one embodiment, is provided a color-coded representation of physical malformation. The availability of physical units can be quantified in bone-specific and suture-specific manner, which facilitates visualization that can support surgical planning application scenarios, skills assessment, pre-operative and post-operative comparisons, and the possibility for real-time visual feedback during performance of the procedure according to intra-operative 3D images.

Surgical planning and simulation: the visualization strategy described above, can support surgical planning. Also, an embodiment of the disclosure uses the model of the patient and the closest normal, and the deformation analysis of the bones, to develop an algorithm that automatically suggests the best cuts and the necessary bone bending. These result in automatic surgical planning, with a number of adjustable parameters (number of cuts, maximum bending, and maximum space between bone grafts). Such predictable outcomes prove to be an improvement in reproducibility and morbidity, while lowering cost.

Validation: according to another embodiment is provided a validation technique that includes: the registration of anatomical correspondence with high precision; a labeling algorithm that has sensitivity and specificity greater than 98%; shape features on the bones/sutures predict craniosynostosis with high significance on a set of 30 patients (with a probability (p) value of $p<0.001$); the suture fusion assessment predicts suture fusion with high significance ($p<0.001$); the model of abnormality shows excellent behavior (symmetric, matches clinicians' intuition) and a diagnostic protocol optimally derived for metopic craniosynostosis that has a diagnostic area under curve (AUC) of 0.998.

Having described the features of the embodiments, the following explains in detail specific embodiments of the present disclosure.

FIG. 1 depicts a flow diagram illustrating the steps performed for constructing a statistical shape model. The shape model is constructed, for example, by taking as input a plurality of reference subjects including both normal and abnormal subjects. According to an exemplary embodiment, a total of 90 normal subjects, 27 subjects with sagittal synostosis, 16 subjects with metopic synostosis, 3 subjects with right coronal synostosis and 5 subjects with left coronal synostosis are considered (for a total of 141 subjects).

In step 101, each input reference subject is subjected to a thresholding process in order to delineate the bone tissue. Specifically, identifying bone tissue in the images reduces to finding an age-adapted threshold since the density of bony tissue appears distinctly in most radiological images. To obtain a 3D representation of the cranium of a subject, the voxels with intensity above 100 Hounsfield units (HU) are labeled, as to avoid all soft tissues (<100 HU) and preserve all cranial tissues. Then the largest connected component of voxels is selected. To obtain a volumetric representation of the bony structures in the cranium but excluding the open sutures (which exhibit a lower density) each subject is subsequently thresholded so that the denser 50% of the sample of bony tissue are kept. Note that the threshold values are evaluated on cases not used in the analysis. As a result of the thresholding process, a volume containing the cranium and another containing the cranial bones with open sutures is obtained.

Figure 4:
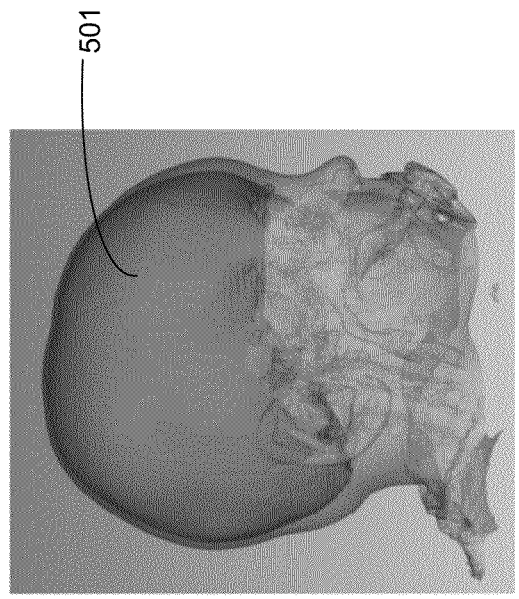
FIG. 4 depicts four landmarks involved in delineating a region of interest in a patient's skull.
Figure 5:
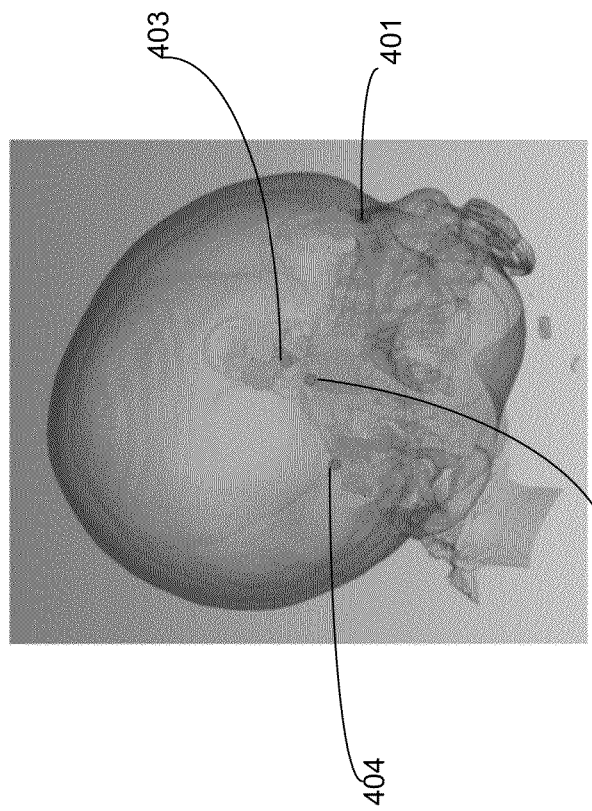
FIG. 5 depicts the region of interest resulting from the landmarks of FIG. 4.

In step 102, each of the reference subjects is subject to normalization via registration process. Shape analysis requires a previous correction of the pose (location, orientation and scale) of each shape instance. According to one embodiment, a head CT image of a healthy subject (the template) is selected in order to define the reference pose. On this template, a set of manual landmarks are selected on structures at the base of the cranium (for instance, the nasion, the opisthion, and the two clinoid processes of the dorsum sellae). Referring to FIG. 4, the nasion is represented as [401], the opisthion is represented as [404] and the two clinoid processes of the dorsum sellae are represented as [402] and [403], respectively. Further, two intersecting planes are defined, one passing through the first three landmarks [401-403], and another passing through the last three [402-404] landmarks, thereby defining a region of interest (ROI), which is represented as [501] in FIG. 5.

Based on the reference template, alignment of all input subjects is performed in order to neutralize their initial pose differences. For each subject, the center of mass of the binary volume is first obtained. A registration procedure is then initialized which includes translating a vector connecting the center of mass for the subject and the template. Note that while doing so, it is assumed that the moments of mass of the structures are similar for both images, which represent the same body part in different patients.

A gradient descent optimization scheme on translation, orientation and scale parameters is further implemented. At each iteration, the employed optimization metric is equivalent to the sum of squared differences (SSD), typically used for registration of binary volumes, which provides a measure of overlap (exclusive-or of the binary voxel sets):

$$SSD(A, B) = \sum_{i=1}^{M} \left(A(i) - \hat{B}\left(i, \vec{\theta}\right)\right)^2, \quad (1)$$

where, A(i) is the template (fixed image) defined over a volume with M elements and evaluated at location i, and $\hat{B}(i, \vec{\theta})$ is the floating image transformed by the set of translation, rotation and scale parameters $\vec{\theta}$, linearly interpolated at i. Note that the metric is computed considering structures in the template that lie inferior to the above described planes passing through the landmarks so as to prevent abnormal anatomy in the cranial region to interfere in the alignment procedure.

As a result of the registration process, a pose-neutral representation of every subject in a common physical frame is obtained. Further, in order to account for age variation, the alignment also includes a scale component. To compare the alignment of every dataset structure, only the base of the skull is considered, precisely below the aforementioned planes defined via landmarks, which are not affected by shape variations due to brain growth and skull malformations. The registration process [102] allows for automatically obtaining of the equivalent landmarks in the patient's image.

On completing the registration process of all the input objects, the shape model process proceeds to step [103], which performs bone labeling of the cranial vault.

The volume representation of the cranial bones with open sutures is used to separate the different cranial bones. Specifically, a graph-cut approach is adopted for the separation of bones at low contact degree interfaces. The term contact degree refers to the number of voxels that belong to a certain bone segment and touch a voxel that belongs to an adjacent bone segment. It serves as a surrogate of suture fusion when the voxels belong to bone segments that are separated by a suture in healthy subjects.

Note that graph-cut techniques are capable of minimizing many sorts of custom energies defined on a graph analogue of an image, and they exhibit good performance and guaranteed convergence (for the binary case) via min-cut/max-flow computation. According to an embodiment, the node structure (graph) is constructed in the following manner.

The node system is constructed from all the voxels in the suture-free bone volume. The subject and the template are first aligned. Then, bones are identified based on a spatial relation between the subject's data and the labels in the template. In order to achieve this, regional cost term is introduced, which, for each label, varies according to the quotient between the distance to the bone with that label in the template, and the distance to the furthest other template bone. The edge cost is fixed and equal for all edges involving different labels.

Note that energy E is defined as the sum over the nodes P of the graph, of a unary and a binary term represented as:

$$E(f) = \alpha \cdot \sum_{p \in P} D_p(f_p) + \sum_{(p,q) \in K} V_{p,q}(f_p, f_q), \quad (2)$$

where, α is a tuning constant parameter, f is a labeling scheme that assigns label $f_p$ to the node p, $D_p(.)$ is a data penalty function that assigns a cost $D_p(f_p)$ to having label $f_p$ at node p, $V_{p,q}(.;.)$ is an interaction potential that assigns cost $V_{p,q}(f_p; f_q)$ to having labels $f_p$ and $f_q$ at nodes p and q, and K is the set of all pairs of neighboring nodes.

Note that in the classical graph flow method, the regional term is formulated in a Bayesian framework as the log-likelihood of obtaining the intensity value of the node from the intensity distribution of a given label, and is represented as follows:

$$D_p(f_p) = -\ln P(I_p|f_p), \quad (3)$$

where $I_p$ is the intensity at node p. Contrary to the classical approach, according to one embodiment, the label energy is defined in terms of a labeling prior. Specifically, if the distance to the cranial bone with label f in the template is $d_f$, the cost of assigning label $f_p$ at node p is computed as follows:

$$D_p(f_p) = d_{f_p} \Big/ \left(d_{f_p} + \max_f(d_f \mid f \neq f_p)\right), \quad (4)$$

and the edge term is computed as:

$$V_{p,q}(f_p, f_q) = \begin{cases} 1 & \text{if } f_p \neq f_q, \\ 0 & \text{otherwise.} \end{cases} \quad (5)$$

Figure 6:
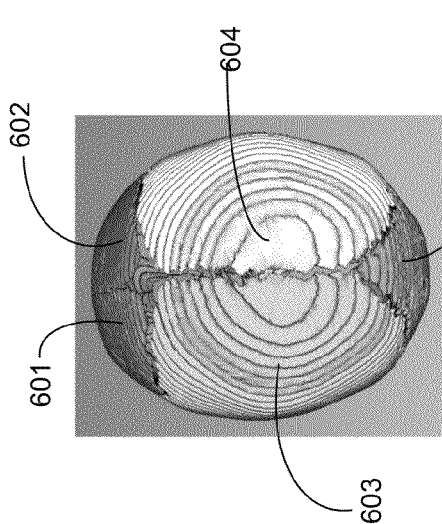
FIG. 6 depicts labeled bone segments of the skull of the patient.

Using the energy from (2), the cut with minimum cost will encourage a separation that assigns labels in accordance to the bone distribution in the template, but at the same time favoring cuts involving minimal numbers of nodes (i.e. at the open sutures). Accordingly, the above graph-cut-based algorithm simultaneously minimizes the number of neighboring volume elements with different bone labels (producing cuts at the sutures) and maximizes the probability of assigning bone labels in accordance to a manually labeled template. The result is a set of identified craniofacial bones as depicted in FIG. 6. Specifically, the left frontal bone is depicted as [601], the right frontal bone is depicted [602], left parietal bone as [603], right parietal bone as [604] and occipital bone as [605] respectively, such that suture-adjacent regions can be obtained at their interfaces.

Figure 7:
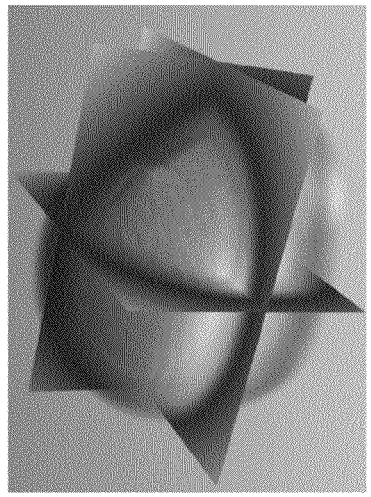
FIG. 7 shows a volumetric rendered normal shape statistical model that encodes variability of normal anatomy across normal subjects.

In step [104], a shape model is computed from the entire set of registered normal subjects, by means of principal component analysis of the normal subjects' Danielsson signed distance function (SDF) volumes. In doing so, embedding of natural shape variation into a statistical shape space representation (as shown in FIG. 7) is achieved. The availability of such a space allows the identification of normal shapes to maximally match the shape of any normal or abnormal anatomy.

Note that local deformation and abnormal curvature is obtained in physical units to facilitate a representation that mimics the mental processes by surgeons in planning cranial shape correction interventions. Such malformation features can be obtained in terms of a subject-specific model of normal anatomy that is obtained from a statistical shape model of normal cranial shapes. According to one embodiment, a total of 90 normal subjects in a 5-fold scheme, resulting in 5 groups of 72 (4 out of 5 normal subjects) instances for training, and remaining 18 (1 out of 5 normal subjects) for testing is used.

An SDF representation for binary volumes of cranial shapes is implemented. Specifically, each normal subject is turned into a high-dimensional vector (as many components as voxels in the volume). The set of all subjects lie on a Riemannian manifold roughly assimilable to a hyper plane. Then PCA is performed on the set of vectors to obtain a 72-dimensional PCA shape space. Note that the first few principal components may capture most of the variation in the space of SDFs, but they do not necessarily capture the variation in the space of the embedded surfaces. Therefore, in the present embodiment, the full set of 72-dimensional PCA space is utilized.

According to an embodiment, the shape space is constructed be using a technique referred to as a constrained projection technique. Specifically, for every test subject, the respective SDF is projected into the PCA shape space. To constrain the resulting projection to lie in the subspace of allowed shapes, the distribution of shapes in the shape space is assumed to follow an independent Gaussian distribution. In doing so, the problem of constructing the shape space translates in bounding each component of the projection to lie in a range extending $\pm 3\sigma$ around the mean shape (origin of the shape space), with $\sigma$ being the standard deviation of each component as computed by the PCA. Furthermore, the constrained projection can be used to reconstruct the SDF and surface model generation techniques can be applied to produce a surface model of tailored normal anatomy for each subject.

According to another embodiment, for each subject a reference normal shape by using the shape space as a multi-atlas, i.e. choosing as shape reference the closest normal shape from the training set of normal cases (closest normal (CN) approach) is computed. The closest normal can be obtained by computing the Mahalanobis distance from the projection to all the projections of all the cases employed for the construction of the shape model, and choosing the closest normal cases as the anatomical reference.

Figure 2:
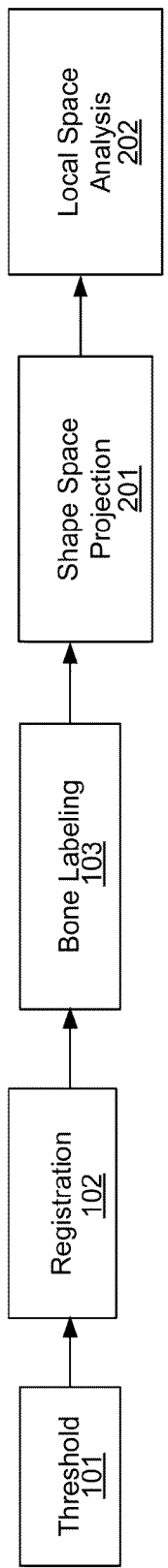
FIG. 2 is a schematic representation of a flow diagram depicting the steps executed for obtaining a deformation field of a patient according to a closest normal subject derived from the shape model.

Having constructed the shape model, all patients' CT scans are subject to the process depicted in FIG. 2. FIG. 2 is a schematic representation of a flow diagram depicting the steps executed for obtaining a deformation field of a patient according to a closest normal subject derived from the shape model. In FIG. 2, the steps of thresholding, normalized registration and bone labeling are similar to those explained with reference to FIG. 1. Thus, a description of these steps is omitted here.

Figure 8:
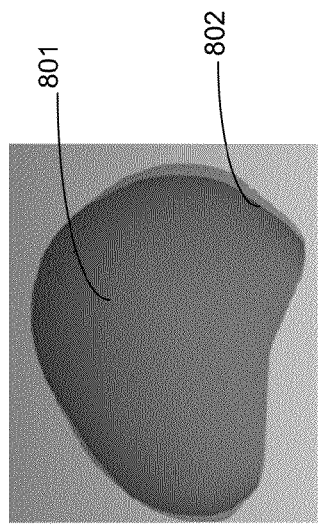
FIG. 8 depicts a model comparing the patient's skull to a closest normal subject that is derived from the normal shape model.

In step [201], the bony tissue of patient is projected into the shape space that is constructed by the method described with reference to FIG. 1. In doing so, the closest normal shape can be obtained by comparing the patient's projection with the projections of all the normal shapes used to build the shape model. Thus, identification of the closest normal shape (represented as [801] in FIG. 8) to the shape of the patient (represented as [802] in FIG. 8) can be obtained, while accounting for the normal variability of anatomy (i.e., ethnicity).

Figure 9:
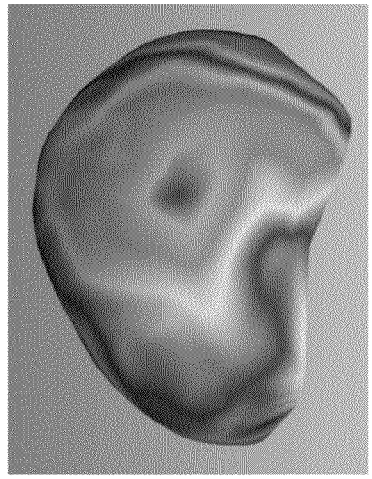
FIG. 9 shows local deformation of the patient's skull from the closest normal shape.

In step [202], a local shape analysis is performed. Once a matched normal shape of the craniofacial bones is obtained, local shape differences between the patient's data ([802]) and the normal shape ([801]) are computed. Robust measures of local shape are derived from deformation fields (such as Hausdorff distance at each point on the skull) and differences in local curvature. This is represented in FIG. 9, wherein the colder colors (e.g., blue/green) represent higher deformation, whereas the warmer colors (red/orange) represent closeness to normal.

Figure 3:
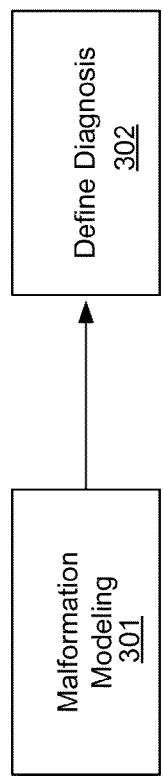
FIG. 3 is a process flow diagram depicting the steps performed for obtaining diagnostic tools derived from modeling malformation across a population of pathologic patients.
Figure 10A:
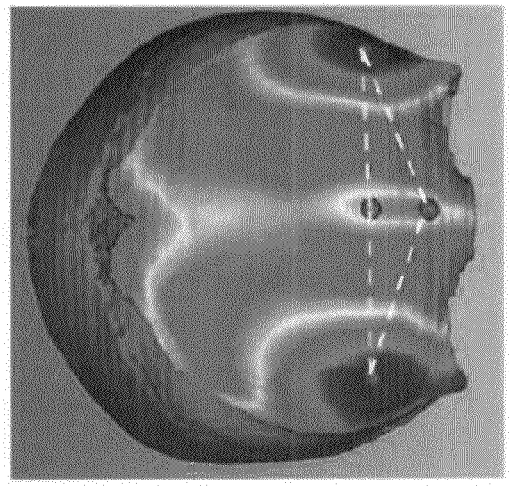
FIG. 10A illustrates an example depicting metopic craniosynostosis and FIG. 10B depicts a pictorial representation of a proxy inter-frontal angle.

FIG. 3 is a process flow diagram depicting the steps performed for obtaining diagnostic tools derived from modeling malformation across a population of pathologic patients. According to an embodiment, diagnostic features for metopic craniosynostosis are described with reference to FIG. 10A.

Once local shape analysis has been performed for a significant number of abnormal subjects (>20), anatomic features are identified that separate in a statistically significant way the abnormal cases from normal subjects. In step [301], the shape analysis results are classified according to the different pathology types to compute models of abnormality. The individual bones are analyzed and precise locations (discussed below) are found that differentiate robustly and reproducibly the aspects of the pathological deviations from normal cases across populations. This results in a visual and geographical chart depicting the degree of local shape abnormality for each pathology as shown in FIG. 10. The average deformation from closest normal across metopic patients is computed so that maximum variation landmarks (represented by solid circles, [●]) can be established, giving rise to optimal diagnostic radiographic measurements (angle between the dotted lines).

In step [302], once the precise locations (landmarks) have been defined, simple measurements (lines and/or angles) can be performed from the landmarks to diagnosis different types of pathology such as metopic craniosynostosis. Note that such measurements can be performed on typical radiological workstations or the like that are available in every clinical environment.

To efficiently diagnose metopic craniosynostosis, it is critical to identify the landmarks in an optimal manner. According to one embodiment, an image repository system including scans for subjects with metopic craniosynostosis with ages 0-12 months is first retrieved. Further, controls can be selected from subjects reported to the emergency room for trauma that had, and were screened in order to exclude, hydrocephalus, intra-cranial tumor, intra-cranial hemorrhage, hardware (e.g. shunts), craniofacial trauma and/or prior craniofacial surgery. Improper protocol studies or poor-quality images can also serve as a criterion for exclusion from subsequent analysis, for example subjects with an axial spacing greater than 5 mm can be excluded.

Further, all subjects are initially aligned to a normal cranial template to correct for scale and pose, using the bones at the skull base. The left and right frontal bones and the metopic suture are then automatically delineated. From the set of aligned normal subjects, a statistical shape model can be constructed as explained previously, and for each metopic subject the deformation fields (distance to the closest normal shape derived from the shape model) can be obtained.

Note that the above methodology also allows finding correspondences between each subject and the template, and obtaining the average deformation field for metopic subjects. For all metopic cases, two lateral landmarks on the left and right frontal bones and one central landmark on the metopic suture are obtained. These landmarks correspond to the point of maximum average malformation in metopic craniosynostosis at each of the three anatomical regions of interest.

As a result, one can measure an optimal inter-frontal angle (OIFA) centered at the landmark on the metopic suture that best describes the recession of the frontal bones and the protrusion of the suture area in trigonocephaly. Note that angular measurements can be obtained by using the Voxar 3D viewer or the like.

According to another embodiment, metopic craniosynostosis can also be measured by defining a proxy inter-frontal angle (PIFA) scheme. In PIFA, the central landmark is replaced by a nearby placed landmark (proxy landmark), wherein the proxy landmark is placed on the same reconstruction plane that contains the two lateral landmarks. As a result of this simplification, the three landmarks can be obtained on the same multi-planar reconstruction, giving rise to a new, easy to obtain, inter-frontal angle which derives from nearly optimal landmarks.

Figure 10B:
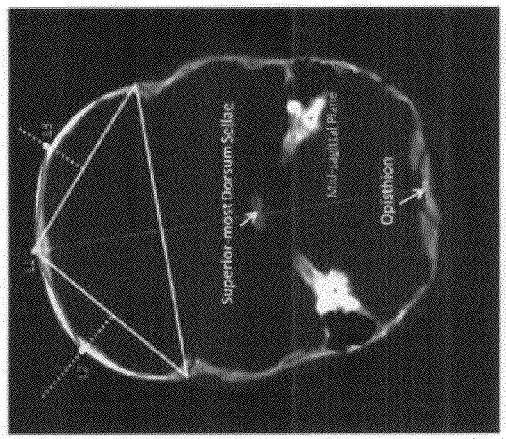

Specifically, PIFA can be obtained as shown in FIG. 10B. First, a multi-planar reconstruction which contains both the opisthion and the most-superior tips of the dorsum sellae, and which is normal to the mid-sagittal plane, is obtained. The central landmark L1 (on the suture), can be found as the most anterior point of the skull in the reconstructed plane. The lateral landmarks L2 and L3 can be found as the most external crossing of the frontal bones with a ray thrown perpendicularly at the mid-point of the line connecting the exterior of the coronal sutures with the central landmark. The PIFA angle (angle formed by the line segment connecting landmark L1 and L2, and the line segment connecting L1 and L3) can be measured by using the Voxar 3D viewer or the like.

According to another embodiment, the shape model described previously can be applied to perform tessellation in craniofacial reconstruction. Specifically, the comparison between abnormal pre-operative shape and the closest normal shape derived from the shape model, can serve as a basis for developing an optimal interventional strategy that can be obtained using a mathematical tessellation algorithm capable of optimizing bone cutting/bending.

Figure 11:
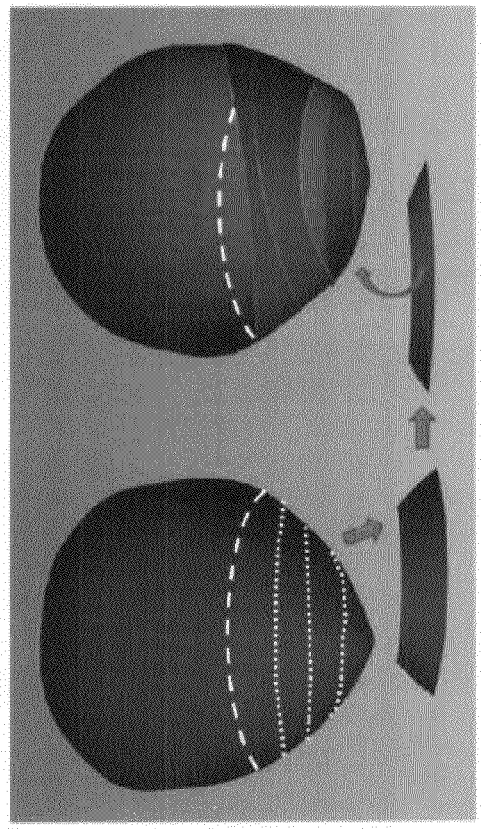
FIG. 11 illustrates the application of tessellation in craniofacial reconstruction.

For instance, upon relying on normalized representations of the patient and the desired normal anatomy, the procedure of surgical reconstruction by bone repositioning and bending can be studied under the light of mathematical tessellation theory. Tessellation theory refers to the field of mathematics that studies the disposition of tessellae (tiles) to cover a specific spatial domain. Analogously, tessellation theory can be used to devise an optimal strategy for surgical reconstruction by indicating the appropriate bone repositioning and bending taking into consideration the patient's anatomy and the reference normal anatomy as shown in FIG. 11.

An optimization scheme can be envisaged, in which the location of the cuts on the subject's surface and the required bending to be applied so that the pieces properly cover the desired shape surface, are iteratively update. This optimization can be constrained by several parameters like the maximum desired number of bone cuts, the maximum acceptable degree of bone bending, and the maximal width of uncovered area between bones in the resulting surface.

Alternatively, the shape model described above can be used in non-surgical shape correction technique such as helmet molding therapy, or cranial orthosis. Helmet molding is a type of treatment where an infant is fitted with a special helmet to correct the shape of the skull. Braces could also be used in the process of non-surgical shape correction.

The above embodiments describe a quantitative description of the synostotic skull so as to provide a full automatic diagnosis. The degree of fusion of the main sutures involved in any of the types of craniosynostosis can be assessed and a full 3D analysis of shape that can quantify deformation according to a precise segmentation of the bone segments in the skull is described. The above embodiments can be implemented on any suitable processing device having an input for data and an output (e.g., display, printer, or the like) to view the diagnosis. Such a processing device can be a commonly used radiological workstation, which is familiar to those skilled in the art and is thus not described herein. The input to the processing device are radiological images (CT scans) or the like that display craniofacial anatomy of both normal and abnormal subjects. Note that in order to define normal anatomy, a large set of images are required (typically greater than 50 subjects across different age and ethnicity groups). However, to execute the methods of the above embodiments, the subjects need to be acquired by the processing device only once. Furthermore, the embodiments described herein are in no manner restricted to be implemented only on a CT system. Other forms of imaging modalities such as MRI, 3D optical/photo scanners, or the like can also be used to obtain images of subjects. Note that employing the embodiments discussed herein, for instance, with an MRI imaging technique also provides the advantageous ability of avoiding radiation exposure issues or the like.

The embodiments discussed herein provide for clinical assessment and a surgical planning tool that can reduce time, subjectivity of assessment, and quantitative guidance for minimally invasive surgical intervention, and post-operative assessment of outcome. Specifically, the embodiments provide for a mechanism that can be used to assess post-operative results and to determine where (location of malformations) and to what extent (degree of malformation) vary from a normal subject, both immediately post-operation as well as with future growth of the skull. Thus, modifications of operative techniques to improve outcomes for both short term and/or long term (growth compensation of the skull) are achieved.

Figure 12:
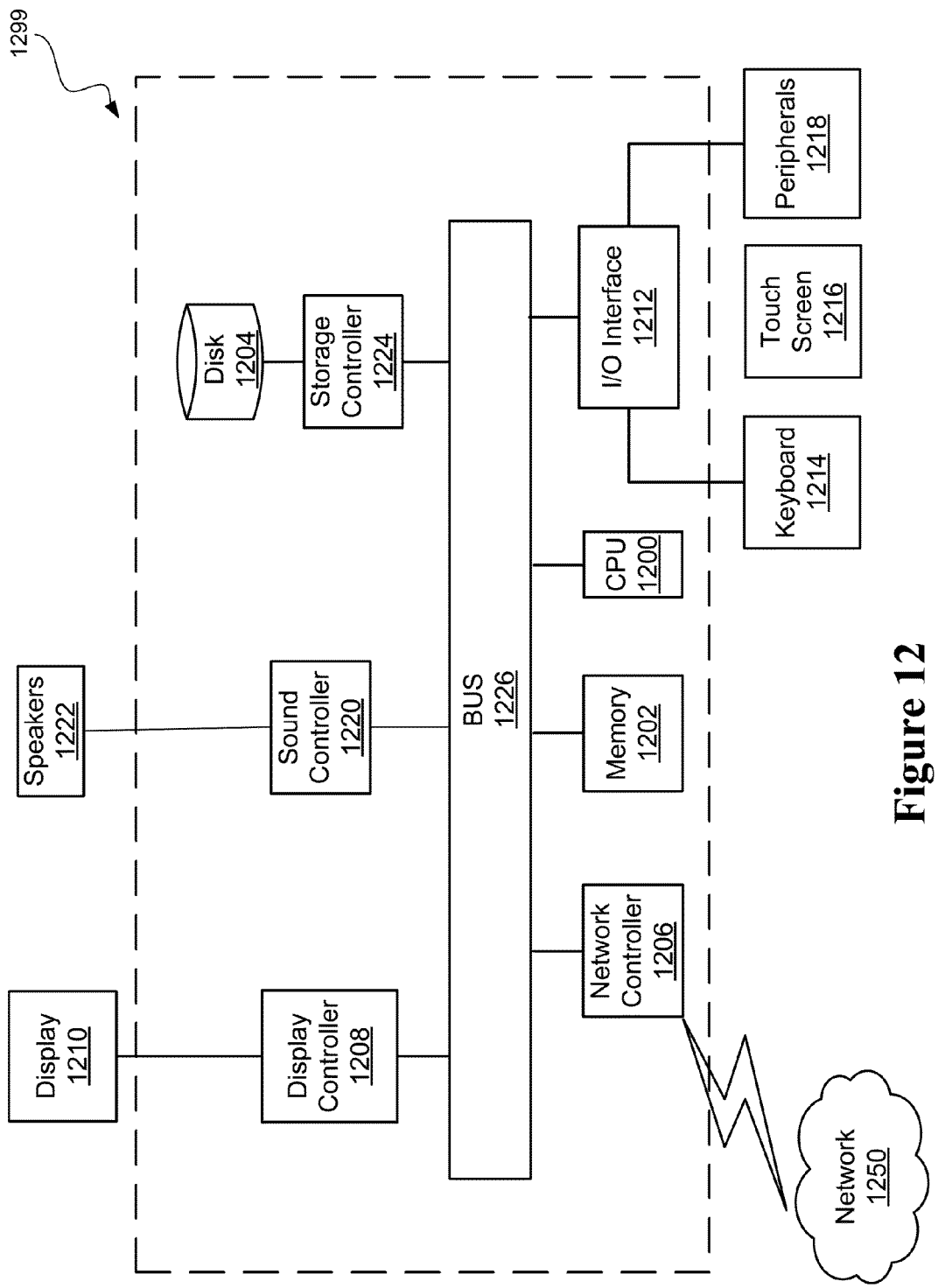
FIG. 12 illustrates a block diagram of a computing device according to one embodiment.

Each of the program or algorithm based elements of the above noted description can be implemented by hardware such as the hardware found in the description of FIG. 12. In FIG. 12, the computer 1299 includes a CPU 1200 which performs the processes described above. The process data and instructions may be stored in memory 1202. These processes and instructions may also be stored on a storage medium disk 1204 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the system communicates, such as a server or computer.

Further, the claimed advancements may be provided as a utility application, background daemon, or component of an operating system, or combination thereof, executing in conjunction with CPU 1200 and an operating system such as Microsoft Windows 7, UNIX, Solaris, LINUX, Apple MAC-OS and other systems known to those skilled in the art.

CPU 1200 may be a Xenon or Core processor from Intel of America or an Opteron processor from AMD of America, or may be other processor types that would be recognized by one of ordinary skill in the art. Alternatively, the CPU 1200 may be implemented on an FPGA, ASIC, PLD or using discrete logic circuits, as one of ordinary skill in the art would recognize. Further, CPU 1200 may be implemented as multiple processors cooperatively working in parallel to perform the instructions of the inventive processes described above.

The computer 1299 in FIG. 12 also includes a network controller 1206, such as an Intel Ethernet PRO network interface card from Intel Corporation of America, for interfacing with network 1250. As can be appreciated, the network 1250 can be a public network, such as the Internet, or a private network such as an LAN or WAN network, or any combination thereof and can also include PSTN or ISDN sub-networks. The network 1250 can also be wired, such as an Ethernet network, or can be wireless such as a cellular network including EDGE, 3G and 4G wireless cellular systems. The wireless network can also be WiFi, Bluetooth, or any other wireless form of communication that is known.

The computer 1299 further includes a display controller 1208, such as a NVIDIA GeForce GTX or Quadro graphics adaptor from NVIDIA Corporation of America for interfacing with display 1210, such as a Hewlett Packard HPL2445w LCD monitor. A general purpose I/O interface 1212 interfaces with a keyboard and/or mouse 1214 as well as a touch screen panel 1216 on or separate from display 1210. General purpose I/O interface also connects to a variety of peripherals 1218 including printers and scanners, such as an OfficeJet or DeskJet from Hewlett Packard. The peripheral elements previously described in the above exemplary embodiments may be embodied by the peripherals 1218 in the exemplary embodiment of FIG. 13.

A sound controller 1220 may also be provided in the computer 1299, such as Sound Blaster X-Fi Titanium from Creative, to interface with speakers/microphone 1222 thereby providing sounds and/or music. The speakers/microphone 1222 can also be used to accept dictated words as commands for controlling the robot-guided medical procedure system or for providing location and/or property information with respect to the target property.

The general purpose storage controller 1224 connects the storage medium disk 1204 with communication bus 1226, which may be an ISA, EISA, VESA, PCI, or similar, for interconnecting all of the components of the robot-guided medical procedure system. A description of the general features and functionality of the display 1210, keyboard and/or mouse 1214, as well as the display controller 1208, storage controller 1224, network controller 1206, sound controller 1220, and general purpose I/O interface 1212 is omitted herein for brevity as these features are known.

Obviously, numerous modifications and variations of the present disclosure are possible in light of the above teachings. It is therefore to be understood that within the scope of the appended claims, the invention may be practiced otherwise than as specifically described herein. For example, advantageous results may be achieved if the steps of the disclosed techniques were performed in a different sequence, if components in the disclosed systems were combined in a different manner, or if the components were replaced or supplemented by other components. For example, certain of the above described techniques and processes could be applied to other parts of the body in addition to the skull, for example, to identify and address deformities in the skeletal structure or to identify and address other medical issues.

The functions, processes and algorithms described herein may be performed in hardware or software executed by hardware, including computer processors and/or programmable processing circuits configured to execute program code and/or computer instructions to execute the functions, processes and algorithms described herein. A processing circuit includes a programmed processor, as a processor includes circuitry. A processing circuit also includes devices such as an application specific integrated circuit (ASIC) and conventional circuit components arranged to perform the recited functions.

The functions and features described herein may also be executed by various distributed components of a system. For example, one or more processors may execute these system functions, wherein the processors are distributed across multiple components communicating in a network. The distributed components may include one or more client and/or server machines, in addition to various human interface and/or communication devices (e.g., display monitors, smart phones, tablets, personal digital assistants (PDAs)). The network may be a private network, such as a LAN or WAN, or may be a public network, such as the Internet. Input to the system may be received via direct user input and/or received remotely either in real-time or as a batch process. Additionally, some implementations may be performed on modules or hardware not identical to those described. Accordingly, other implementations are within the scope that may be claimed.

It should be noted that, as used in the specification and the appended claims, the singular forms "a," "an," and "the" include plural referents unless the context clearly dictates otherwise.

What is claimed is:

1. A method for assessing craniofacial malformations, the method comprising:

receiving imaging data containing craniofacial anatomy of a plurality of subjects, the plurality of subjects including subjects of a first type and subjects of a second type;

delineating bone tissue for each subject of the plurality of subjects from the received imaging data;

registering the delineated bone tissue for each subject of the plurality of subjects to a reference space;

identifying craniofacial bones for each subject of the plurality of subjects for which the registering has been performed;

computing a shape model based on the identified craniofacial bones of only the first type of subjects;

deriving, based on the computed shape model, for each subject of the plurality of subjects, a normal shape closest to a shape of the respective subject; and assessing for each subject of the plurality of subjects, a shape difference between the shape of the respective subject and the closest derived normal shape.

2. The method of claim 1, further comprising:

classifying for each subject of the second type, the shape difference between the shape of the respective subject and the closest derived normal shape to the respective subject into a chart including a plurality of pathology types and a degree of shape abnormality;

assessing fusion of sutures for each subject of the second type; and using the chart to diagnose a pathology.

3. The method of claim 1, wherein the plurality of subjects includes subjects of different ages and ethnicities.

4. The method of claim 1, wherein the registering is performed using a scale component to account for age variation.

5. The method of claim 1, wherein the reference space includes a craniofacial anatomy of a healthy subject.

6. The method of claim 1, wherein the registering includes aligning each subject of the plurality of subjects to the reference space based on a base of a skull anatomy and predetermined landmarks in the reference space.

7. The method of claim 1 further comprising:

diagnosing metopic craniosynostosis based on computing three landmarks in a region of interest in a skull anatomy of the subject; and computing an angle representing a degree of metopic craniosynostosis, the angle formed between two lines connecting the three computed landmarks.

8. The method of claim 7, wherein the computed landmarks correspond to points on the skull anatomy of the subject of the second type.

9. The method of claim 1, further comprising:

planning a skull reconstruction based on a predetermined number of identified landmarks on the skull and the shape difference between the respective subject and the closest derived normal shape to the respective subject; and performing tessellation of the skull based on the predetermined number of identified landmarks and the shape difference.

10. The method of claim 1, further comprising:

performing post-operative assessment and evaluation of a quality of surgery based on the closest derived normal shape to the respective subject.

11. The method of claim 1, wherein the identifying craniofacial bones for each subject of the plurality of subjects is performed by a graph-cut based algorithm and the computing of the shape model is performed by principal component analysis.

12. The method of claim 1, further comprising:

diagnosing one of a sagittal craniosynostosis, a coronal craniosynostosis and a lambdoid craniosynostosis based on the shape difference between the shape of the respective subject and the closest derived normal shape to the respective subject.

13. The method of claim 1, wherein the imaging data is radiological data, X-ray data, computed tomography data, ultrasound data, or data generated by magnetic resonance imaging, 3D photogrammetry, optical imaging, or by surface laser images.

14. The method of claim 1, wherein the computed shape model encodes variability in craniofacial anatomy of the first type of subjects.

15. The method of claim 1, wherein the delineating further comprises:

generating, a first volumetric representation corresponding to a surface of the cranium of the subject, and a second volumetric representation including cranial bones and open sutures included in the cranium of the subject.

16. An image processing device comprising:

circuitry configured to receive imaging data containing craniofacial anatomy of a plurality of subjects, the plurality of subjects including subjects of a first type and subjects of a second type;

delineate bone tissue for each subject of the plurality of subjects from the received imaging data;

register the delineated bone tissue for each subject of the plurality of subjects to a reference space;

identify craniofacial bones for each registered subject of the plurality of subjects;

compute a shape model based on the identified craniofacial bones of only the first type subjects;

derive based on the computed shape model, for each subject of the plurality of subjects, a normal shape closest to a shape of the respective subject; and assess for each subject of the plurality of subjects, a shape difference between the shape of the respective subject and the closest derived normal shape.

17. The image processing device of claim 16, wherein the circuitry is further configured to classify, for each subject of the second type, the shape difference between the shape of the respective subject and the closest derived normal shape to the respective subject, into a chart including a plurality of pathology types and a degree of shape abnormality;

assess fusion of sutures for each subject of the second type; and use the chart to diagnose a pathology.

18. The image processing device of claim 16, wherein the circuitry is further configured to align each subject of the plurality of subjects to the reference space based on a base of a skull anatomy and predetermined landmarks in the reference space.

19. The image processing device of claim 16, wherein the circuitry is further configured to diagnose metopic craniosynostosis based on computing three landmarks in a region of interest in a skull anatomy of the subject; and compute an angle representing a degree of metopic craniosynostosis, the angle formed between two lines connecting the computed landmarks.

20. The image processing device of claim 16, wherein the circuitry is further configured to identify craniofacial bones for each subject of the plurality of subjects by a graph-cut based algorithm and compute the shape model by using principal component analysis.

21. The image processing device of claim 16, wherein the imaging data is radiological data, X-ray data, computed tomography data, ultrasound data, or data generated by magnetic resonance imaging, 3D photogrammetry, optical imaging, or by surface laser images.

22. A non-transitory computer readable medium having stored thereon a program that when executed by a computer causes the computer to execute a method comprising:

receiving imaging data containing craniofacial anatomy of a plurality of subjects, the plurality of subjects including subjects of a first type and subjects of a second type;

delineating bone tissue for each subject of the plurality of subjects from the received imaging data;

registering the delineated bone tissue for each subject of the plurality of subjects to a reference space;

identifying craniofacial bones for each subject of the plurality of subjects for which the registering has been performed;

computing a shape model based on the identified craniofacial bones of only the first type of subjects;
deriving, based on the computed shape model, for each subject of the plurality of subjects, a normal shape closest to a shape of the respective subject; and
assessing for each subject of the plurality of subjects, a shape difference between the shape of the respective subject and the closest derived normal shape.

23. The non-transitory computer readable medium of claim 22, wherein the method further comprising:
classifying for each subject of the second type, the shape difference between the shape of the respective subject and the closest derived normal shape to the respective subject into a chart including a plurality of pathology types and a degree of shape abnormality;
assessing fusion of sutures for each subject of the second type; and
using the chart to diagnose a pathology.

24. The non-transitory computer readable medium of claim 23, the method further comprising:
performing post-operative assessment and evaluation of a quality of surgery based on the closest derived normal shape to the respective subject.

25. The non-transitory computer readable medium of claim 23, the method further comprising:
diagnosing one of a sagittal craniosynostosis, a coronal craniosynostosis and a lambdoid craniosynostosis based on the shape difference between the shape of the respective subject and the closest derived normal shape to the respective subject.

26. The non-transitory computer readable medium of claim 22, the method further comprising:
diagnosing metopic craniosynostosis based on computing three landmarks in a region of interest in a skull anatomy of the subject; and
computing an angle representing a degree of metopic craniosynostosis, the angle formed between two lines connecting the three computed landmarks.

27. The non-transitory computer readable medium of claim 22, the method further comprising:
planning a skull reconstruction based on a predetermined number of identified landmarks and the shape difference between the respective subject and the closest derived normal shape to the respective subject; and
performing tessellation of the skull based on the predetermined number of identified landmarks and the shape difference.

28. The non-transitory computer readable medium of claim 22, wherein the identifying craniofacial bones for each subject of the plurality of subjects is performed by a graph-cut based algorithm and the computing of the shape model is performed by principal component analysis.

29. The non-transitory computer readable medium of claim 22, wherein the imaging data is radiological data, X-ray data, computed tomography data, ultrasound data, or data generated by magnetic resonance imaging, 3D photogrammetry, optical imaging, or by surface laser images.

* * * * *